United States Patent [19]

Patterson

[11] 4,210,027
[45] Jul. 1, 1980

[54] METHOD FOR DETERMINATION AND GRADING OF PRECIOUS MINERALS

[75] Inventor: James A. Patterson, Los Altos, Calif.

[73] Assignee: Specific Volume Systems, Inc., Mountain View, Calif.

[21] Appl. No.: 959,673

[22] Filed: Nov. 13, 1978

[51] Int. Cl.² ............................................. G01N 33/20
[52] U.S. Cl. .................................................. 73/432 R
[58] Field of Search ............. 73/32 R, 432 R; 75/100, 75/118 R

[56] References Cited

PUBLICATIONS

Phillips, H. J., *Gold Assaying–A Practical Handbook*, Crosby Lockwood & Son, London 1904, pp. 71–72.

*Primary Examiner*—Gerald Goldberg
*Assistant Examiner*—Joseph W. Roskos
*Attorney, Agent, or Firm*—Limbach, Limbach & Sutton

[57] ABSTRACT

A method is disclosed for determining the amount of a precious metal, such as gold, in an object such as a gold nugget. The method uses certain specific volume techniques together with known properties of gold and other materials in carrying out the claimed invention.

1 Claim, 1 Drawing Figure

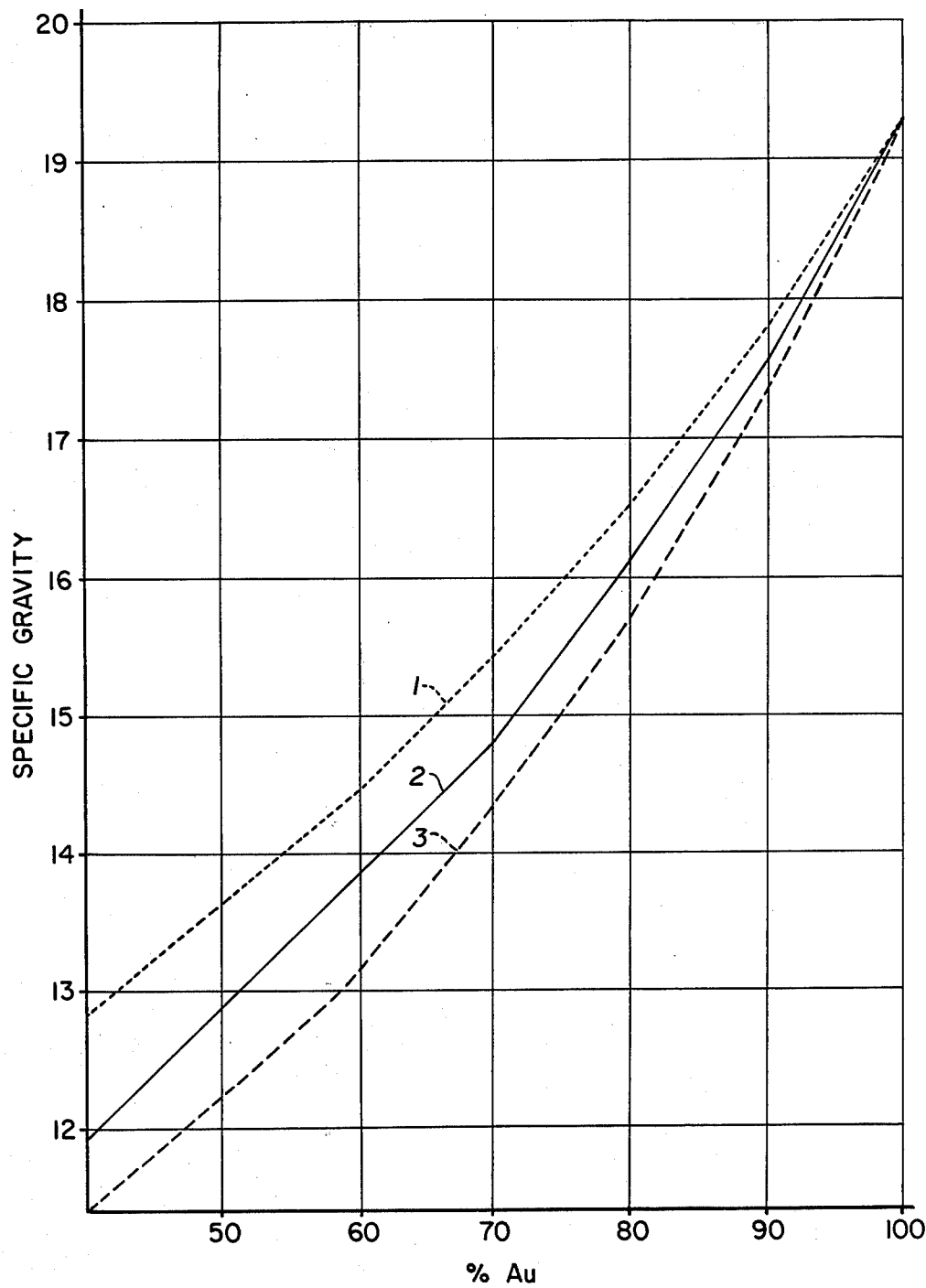

METHOD FOR DETERMINATION AND GRADING OF PRECIOUS MINERALS

BACKGROUND OF THE INVENTION

It is found to have been extremely difficult to determine the amount of a precious metal in an object without destroying the object involved. For example, natural gold nuggets are used in jewelry and as collector's items. A method was sought which could determine whether or not the nugget was natural and made of gold without destroying the nugget in the process.

Natural gold nuggets have a fineness which is above 700. However, the density of the nugget may be lower than that required for 700 fine gold. In attempting to analyze the nugget in the past, the following tests were generally performed:
1. Inspection of general appearance and color.
2. Surface grazing.
3. Permanent color-wipe test.
4. Presence of quartz.
5. Magnetic characteristics.
6. Surface bubbling of heated nugget.
7. Testing the surface depth hardness with, for example, a gauge drill.
8. Drilling the sample to determine color and use of drill filing material in spectrographic tests.
9. Acid treatment.
10. Melting temperature.

The majority of tests which are outlined above in some way injure or completely destroy the nugget. For example, one cannot adequately determine the melting point of a nugget without actually melting the entire nugget or a piece thereof. Once this is done, the aesthetic value of the product is destroyed although the gold value remains the same. This is smilarly true with surface grazing, surface bubbling, drilling and acid treatment.

It is thus an object of the invention to determine whether or not an object such as a gold nugget is natural.

It is a further object of the present invention to determine whether or not a nugget is natural and the quality of gold found therein without practicing the tests which can harm or destroy the nugget as outlined above.

SUMMARY OF THE INVENTION

Gold nuggets are primarily composed of a homogeneous alloy of gold, silver and copper, the percentages of silver and copper determining the characteristic color of the nugget. For example, rose gold is high in copper while yellow gold generally has an approximately 50—50 copper to silver ratio. Green gold is traditionally high in silver, while white gold has a 55-50 silver to copper/nickel alloy ratio. Nuggets further characteristically have a high percent of quartz contained as a non-homogeneous mineral running throughout the nugget body. Thus, the initial determinations to be made are (1) the amount of quartz in the nugget body and (2) the approximate quantity of secondary elements, such as silver, copper and nickel, which have alloyed with the gold.

DETERMINATION OF QUARTZ CONTENT

Large nuggets have a considerable amount of embedded quartz. Naturally, it is virtually impossible to determine the exact amount of quartz embedded in a nugget without destroying the nugget itself. It has been found, however, that by practicing the method of the present invention, a surprisingly accurate means of estimating the approximate quantity of quartz within a nugget can be carried out. This is done by determining the approximate percent surface area of quartz found on the nugget surface and using this percentage to approximate the percent volume of quartz within the nugget body.

The nugget is first placed face down on a piece of carbon paper which has been placed over square-ruled paper. The outline of the nugget face is traced onto the carbon paper which provides a corresponding tracing upon the square-ruled paper. The nugget is then removed from the carbon paper and a piece of thin tissue paper is placed upon the same surface and the quartz area, which shows through the tissue paper, is traced directly onto the tissue paper. The tissue paper is then placed upon the carbon paper and the outline of the quartz area retraced onto the carbon paper, resulting in a corresponding image appearing on the square-ruled paper. By counting the respective squares and comparing the total nugget face area to the quartz area, one can arrive at a reasonably accurate ratio of quartz weight to total nugget weight. This determination can be made for each face of the nugget in order to arrive at a more accurate determination.

The fraction of quartz by volume within the nugget has been determined. The entire nugget volume can be accurately determined by use of the SVS method, which is disclosed in co-pending application Ser. No. 959,677, filed Nov. 13, 1978 entitled Specific Volume Determining Method And Apparatus the disclosure of which is herein incorporated by reference. The weight of quartz is subtracted from the weight of the entire nugget by knowing the percent quartz within the nugget (calculated previously) and the specific gravity of quartz which is 2.60 g/cc. By subtracting the volume and weight of quartz from that of the total nugget, one arrives at the density of the nugget less the primary non-homogeneous impurity, quartz.

DETERMINATION OF ALLOY COMPOSITION

The specific gravity of pure gold is 19.3 g/cc. The specific gravity of an alloy made of gold, silver, copper and/or nickel is somewhat less than that of pure gold.

The FIGURE shows a graph of the specific gravity of an object, such as a nugget, versus the percent gold found therein. There are actually three curves, Curve 2 representing the relationship between the specific gravity and percent gold for yellow gold, i.e., having gold alloyed with a 50 to 50 ratio of silver to copper. Curve 1 depicts the relationship between specific gravity and percent gold for green gold, i.e., gold alloyed with silver. Curve 3 depicts the relationship between specific gravity and percent gold for red or rose gold, i.e., gold being alloyed with copper.

As stated previously, gold nuggets are primarily composed of alloys of gold, silver and copper with white gold having some nickel found therein. Thus, a visual inspection of the nugget is first carried out to determine the primary alloyed metal. If the nugget is primarily yellow in color, then the alloy is substantially a 50 to 50 silver to copper alloy. If the nugget is white in color, the alloy is primarily 50 to 50 silver to copper/nickel alloy; while if the nugget is green or red in color, silver or copper, respectively, are alone alloyed with gold. Many times an alloy will have traces of various types of gold in a single chunk. For example, a single nugget might have both yellow and green gold which would indicate some 50 to 50 silver to copper alloy and pure silver alloyed with gold.

The specific gravity of the nugget was determined as previously described. To briefly restate the technique, the volume and weight of the total nugget was determined and the volume and weight of the embedded quartz was also calculated. The volume and weight of the quartz was then subtracted from corresponding values of the total nugget and the specific gravity of the nugget calculated by dividing the weight of the nugget by the unit volume in grams per cubic centimeter. One can then go to the figure and finding the specific gravity on the vertical axis, go over to the proper curve on the graph and go down to the horizontal axis to determine the percent gold in the nugget. As stated, there are only three curves depicted, i.e., those for yellow, green and red gold. White gold has a specific gravity very close to that of yellow gold for copper has a density of 8.96 g/cc and nickel has a density of 8.90 g/cc so that both curves would virtually fall on one another in the depicted figure. Also, because nuggets may many times possess characteristics of various types of gold, the practitioner must extrapolate between the figures to achieve the most accurate gold content. For example, if a nugget has traces of yellow and green gold, one would look someplace between Curve 1 and Curve 2 to improve the accuracy of the estimation. This is not viewed as a serious problem for as the purity of the gold increases, all the curves become closer to one another and any errors due to poor estimations would minimize. Even at relatively low gold contents, an error in extrapolation between Curves 1 and 2 would probably only result in a deviation in percent gold of about 5 percent.

By practicing the present invention, one can determine, with a reasonable degree of accuracy, the percent gold in an article, such as a gold nugget, without employing any of the prior art techniques which generally result in at least partial destruction of the nugget structure. Briefly recited, this is simply done by estimating the percentage of copper, silver and nickel alloyed with the gold in the nugget by visual inspection. One will then determine the volume and weight of quartz in the nugget, subtract the volume and weight of quartz from the volume and weight of the total nugget, which would directly yield the specific gravity of the alloy. This in turn, would directly yield the percent gold in the total nugget.

What is claimed is:

1. A method of determining the amount of gold in a nugget comprising:
   a. measuring the weight and volume of the nugget;
   b. determining the weight and volume of quartz in the nugget by calculating the approximate percentage of surface area of quartz on the surface of the nugget and multiplying this percentage by the volume of the nugget wherein the surface area of the quartz to the surface area of the entire nugget is determined by:
      1. placing the nugget face down on a piece of carbon paper overlaying a square-ruled paper;
      2. tracing the outline of the nugget face onto carbon paper which forms an outline of the face of the nugget on the square-ruled paper;
      3. tracing the outline of the quartz area on the nugget face using substantially transparent tracing paper;
      4. transferring the outline on the tracing paper to the square-ruled paper through the carbon paper;
      5. comparing the area of the nugget surface with the area of the quartz; and
      6. repeating steps 1–5 for each face of the nugget and averaging the calculated values;
   c. subtracting the volume and weight of the quartz from the volume and weight of the total nugget to yield the specific gravity of gold alloy within the nugget;
   d. estimating the percentage of copper, silver and nickel alloyed with the gold in the nugget; and
   e. comparing the specific gravity of the alloy with the percentage of copper, silver and nickel to yield the total amount of gold.

* * * * *